(12) United States Patent
Lee et al.

(10) Patent No.: US 6,410,670 B1
(45) Date of Patent: Jun. 25, 2002

(54) PHOTORESIST MONOMER HAVING HYDROXY GROUP AND CARBOXY GROUP, COPOLYMER THEREOF AND PHOTORESIST COMPOSITION USING THE SAME

(75) Inventors: Geun Su Lee; Cha Won Koh; Jae Chang Jung; Min Ho Jung; Ki Ho Baik, all of Kyoungki-do (KR)

(73) Assignee: Hyundai Electronics Industries Co., Ltd. (KR)

( * ) Notice: Subject to any disclaimer, the term of this patent is extended or adjusted under 35 U.S.C. 154(b) by 0 days.

(21) Appl. No.: 09/383,861

(22) Filed: Aug. 26, 1999

(30) Foreign Application Priority Data

Aug. 26, 1998 (KR) .......................................... 98-34694
Sep. 21, 1998 (KR) .......................................... 98-39079

(51) Int. Cl.$^7$ .......................... C08J 132/08; C08J 34/00

(52) U.S. Cl. .................. 526/281; 526/282; 526/258; 526/271; 526/272; 526/219.6; 430/296; 430/270; 430/192

(58) Field of Search ................................. 526/282, 281, 526/219.6, 271, 258, 313, 272; 430/296, 192, 270

(56) References Cited

U.S. PATENT DOCUMENTS

| | | | |
|---|---|---|---|
| 3,370,047 A | 2/1968 | Raines | 260/78.5 |
| 3,715,330 A | 2/1973 | Nogami et al. | 260/40 R |
| 4,011,386 A | 3/1977 | Matsumoto et al. | 526/259 |
| 4,106,943 A | 8/1978 | Ikeda et al. | 96/115 R |
| 4,126,738 A | 11/1978 | Gaylord | 526/271 |
| 4,202,955 A | 5/1980 | Gaylord | 526/272 |
| 4,440,850 A | 4/1984 | Paul et al. | 430/325 |
| 4,491,628 A | 1/1985 | Ito et al. | 430/176 |
| 4,857,435 A | 8/1989 | Hopf et al. | 430/192 |
| 4,883,740 A | 11/1989 | Schwalm et al. | 430/270 |
| 4,948,856 A | 8/1990 | Minchak et al. | 526/281 |
| 4,986,648 A | 1/1991 | Kobayashi et al. | 351/160 R |
| 5,064,919 A | 11/1991 | Hara et al. | 526/169 |
| 5,087,677 A | 2/1992 | Brekner et al. | 526/160 |
| 5,212,043 A | 5/1993 | Yamamoto et al. | 430/192 |
| 5,252,427 A | 10/1993 | Bauer et al. | 430/270 |
| 5,278,214 A | 1/1994 | Moriya et al. | 524/238 |
| 5,324,804 A | 6/1994 | Steinmann | 526/313 |
| 5,585,219 A | 12/1996 | Kaimoto et al. | 430/270.1 |
| 5,738,975 A | 4/1998 | Nakano et al. | 430/280.1 |
| 5,843,624 A | 12/1998 | Houlihan et al. | 430/296 |
| 5,849,808 A | 12/1998 | Schacht et al. | 522/31 |
| 5,866,665 A | 2/1999 | Shaffer et al. | 526/348.4 |
| 6,028,153 A | 2/2000 | Jung | 526/258 |
| 6,045,967 A | 4/2000 | Jung et al. | 430/270.1 |

FOREIGN PATENT DOCUMENTS

| | | | |
|---|---|---|---|
| EP | 0071571 | 7/1982 | |
| EP | 0 291 970 | 5/1988 | |
| EP | 0789278 A2 | 2/1997 | |
| EP | 794458 A2 | 9/1997 | |
| EP | 0836119 A1 | 11/1997 | |
| EP | 0878738 A2 | 11/1998 | ........... G03F/7/004 |
| GB | 0768813 | 2/1957 | |
| GB | 1329997 | 9/1970 | |
| GB | 1342112 | 12/1973 | |
| GB | 1484061 | 8/1977 | |
| GB | 1484061 | 8/1997 | .............. C08J/3/28 |
| GB | 1335095 | 10/1997 | |
| GB | 2320501 A | 6/1998 | |
| GB | 2320717 A | 7/1998 | |
| GB | 2320718 A | 7/1998 | |
| GB | 2321060 A | 7/1998 | |
| GB | 2332679 A | 6/1999 | ......... C08F/232/08 |
| GB | 2336845 A | 11/1999 | ......... C08F/222/06 |

(List continued on next page.)

OTHER PUBLICATIONS

WPI Abstract No. 99–076491 & JP 10316720, Feb. 12, 1998, Japan.

Jae–Chang Jung et al., "ArF Single Layer Resist Composed of Alicyclic Main Chain Containing Maleic Anhydride," *Journal of Photopolymer Science and Technology*, vol. 10, No. 4 (1997), pp. 529–534.

(List continued on next page.)

*Primary Examiner*—David W. Wu
*Assistant Examiner*—Tanya Zalukaeva
(74) *Attorney, Agent, or Firm*—Townsend and Townsend and Crew LLP

(57) ABSTRACT

The present invention relates to novel monomers and their polymers, which are useful in a photolithography employing a light source in the far ultraviolet region of the light spectrum, copolymers thereof, and photoresist compositions prepared therefrom. Photoresist monomers of the present invention are represented by the following Chemical Formula 1:

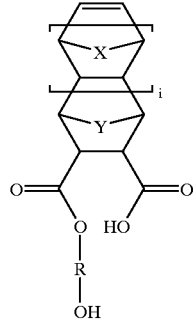

Chemical Formula 1 wherein, R is substituted or non-substituted linear or branched ($C_1$–$C_{10}$)alkyl, substituted or non-substituted ($C_1$–$C_{10}$)ether, substituted or non-substituted ($C_1$–$C_{10}$)ester, or substituted or non-substituted ($C_1$–$C_{10}$)ketone; X and Y are independently $CH_2$, $CH_2CH_2$, oxygen or sulfur; and i is 0 or an integer of 1 to 2.

9 Claims, No Drawings

U.S. PATENT DOCUMENTS

| GB | 2336846 A | 11/1999 | ......... C08F/222/40 |
|----|-----------|---------|----------------------|
| NL | 128164 | 2/1977 | |
| NL | 1010914 | 8/1999 | |
| WO | WO 96/37526 | 11/1996 | |
| WO | WO 97/06216 | 2/1997 | ............ C09D/5/00 |
| WO | WO 97/33198 | 9/1997 | |
| WO | WO 98/07759 | 2/1998 | ............. G08F/2/50 |
| WO | WO 99/14256 | 3/1999 | |

OTHER PUBLICATIONS

Kaichiro Nakano, et al., "Chemically Amplified Resist Based on High Etch–Resistant Polymers for 193–nm Lithography," *Journal of Photopolymer Science and Technology*, vol. 10, No. 4 (1997), pp. 561–570.

R.D. Allen et al., "The Influence of Photoacid Structure on the Design and Performance of 193nm Resists," 1997, *Journal of Photopolymer Science and Technology*, vol. 10, 503–510.

F.M. Houlihan et al., "A Commercially Viable 193nm single Layer Resist Platform," 1997, *Journal of Photopolymer Science and Technology*, vol. 10, 511–520.

Thomas I. Wallow, et al., "Evaluation of Cycloolefin–Maleic Anhydride Alternating Copolymers as Single–Layer Photoresist for 193nm Photolithography," *Proc. SPIE*, vol. 2724, 1996, pp. 355–364.

T. Hattori et al., "Synthesis and Dissolution Characteristics of Novel Alicyclic Polymer With Monoacid Ester Structures," *Journal of Photopolymer Science and Technology*, vol. 10, 1997, pp. 535–544.

K. Nozaki and Ei Yaro, "New Protective Groups in Methacrylate Polymer for 193–nm Resists," *Journal of Photopolymer Science and Technology*, vol. 10, 1997, pp. 545–550.

Alexander A. Dobrev et al., "First Application of Functionalized in the Ester Moiety Acrylates in Diels–Alder Reaction: Influence of Solvents on Stereochemistry," *Bulgarian Chemical Communications*, vol. 28, No. 2 (1995) pp. 253–258.

T.P McGovern et al., "Mosquito Repellents: Monocarboxylic Esters of Aliphatic Diols;" *Journal of the American Mosqito Control Association*, vol. 4, No. 3, pp. 314–321.

S.J. Choi et al., "New ArF Single–layer Resist for 193–nm Lithography", 1997, Journal of Photopolymer Science and Technology, vol. 10, 521–528.

CA Abstract No. 104:149512 & Macromolecules 19(4) 1266–8 (1986).

CA Abstract No. 91:124064 & Makromol. Chem. 180(8) 1975–88 (1979).

CA Abstract No. 113:24734 & JP 02 051511.

CA Abstract No. 127:227269 & J Photopolym. Sci. Technol. 10(4) 529–534 (1997).

CA Abstract No. 124:317926 & Marcomol. Rapid Commun. 17(3) 173–180 (1996).

CA Abstract No. 124:203171 & Macromolecules 29(8) 2755–63 (1996).

CA Abstract No. 127:227308 & Proc. SPIE–Int. Soc. Opt. Eng. (1997) 3049 Advances in Resist Technology and Processing XIV 92–103.

CA Abstract No. 66:18889 & Magy. Kem. Foly. (1966) & 72(11)491–3.

CA Abstract No. 199328–07–9.

CA 1981:47831 Vesti Akad, Navuk BSSR, Ser. Khim. Navuk (1980) 5, pp. 128–30.

U.S. application No. 08/896,768, Jung et al., filed Jul. 18, 1997.

U.S. application No. 08/992,033, Jung et al., filed Dec. 17, 1997.

U.S. application No. 09/000,984, Jung et al., filed Dec. 30, 1997.

U.S. application No. 09/152,976, Jung et al., filed Sep. 14, 1998.

U.S. application No. 09/222,053, Jung et al., filed Dec. 29, 1998.

U.S. application No. 09/223,510, Jung et al., filed Dec. 30, 1998.

U.S. application No. 09/223,662, Jung et al., filed Dec. 30, 1998

U.S. application No. 09/301,944, Jung et al., filed Apr. 29, 1999.

U.S. application No. 09/301,945, Jung et al., filed Apr. 29, 1999.

U.S. application No. 09/302,064, Lee et al., filed Apr. 29, 1999.

U.S. application No. 09/311,488, Jung et al., filed May 13, 1999.

U.S. application No. 09/360,402, Jung et al., filed Jul. 23, 1999.

U.S. application No. 09/383,547, Jung et al., filed Aug. 26, 1999.

U.S. application No. 09/383,475, Roh et al., filed Aug. 26, 1999.

Japanese Abstract Pub. 05297591 pub. Nov. 12, 1993 for Applicationb No. 04099967 Apr. 1992.

D. Braun and Joannis Pomakis, Uber Die Copolymerisation von Maleinsaureanhydrid Mit Bicyclo [2.2.1] Hept–5–En–2–Carbonsaure, *European Polymer Journal*, (1974) vol. 10 [4] pp. 357–365. (Abstract only in English).

J. Byers et al., Recent Advancements in Cycloolefen Based Resists for ArF Lithography, *Journal of Photopolymer Science and Technology*, (1998) vol. II No. 3, pp. 465–474.

James V. Crivello and Sang–Yeon Shim, Chemically Amplified Electron–Beam Photoresists, *Chemical Mater.*, (1996) vol. 8, pp. 376–381.

F.M. Houlihan et al., Photo Generators of Sulfamic Acids; Use in Chemically Amplified Single Layer Resists, *Journal of Photopolymer Science and Technology* (1998) vol. 11, No. 3, pp. 419–430.

35–Synthetic High Polymers, *Chemical Abstracts*, (1967) vol. 66, 76325, pp. 7178–7179.

WPI Accession No. 94–227160[28] (FR2695540).

WPI Accession No. 90–049159 [07] (JP2003404 (elf)).

WPI Accession No. 99–076491 (JP10316720).

Japanese Patent Abstract 10017526.

Japanese Patent Abstract 08134015 A.

CA 121:10910 (JP 05310885).

CA 129:209337 (JP 10–218941).

CA 129:223219 (JP 10213912).

CA 1981–47831.

Uzodinma Okoroanyanwu et al., New Single Layer Positive Photoresists for 193 nm Photolithography, *SPIE*, vol. 3049, 1997, pp. 92–103.

CA 130:229879.

ACS Abstract Ref. 172992–05–1.

PHOTORESIST MONOMER HAVING HYDROXY GROUP AND CARBOXY GROUP, COPOLYMER THEREOF AND PHOTORESIST COMPOSITION USING THE SAME

FIELD OF THE INVENTION

The present invention relates to novel monomers used for preparing a photoresist copolymer, copolymers thereof, and photoresist compositions prepared therefrom. More specifically, it relates to such novel monomers, copolymers and photoresist compositions suitable to be exposed to light in the far ultraviolet region of the spectrum.

BACKGROUND OF THE INVENTION

A photosensitive film for use with far ultraviolet light, in particular, for ArF radiation, must satisfy several requisites; it must have low light absorbance at a wavelength of 193 nm, excellent etching resistance and adhesiveness to a substrate, and be developable in an aqueous solution of 2.38% or 2.6% tetramethylammonium hydroxide (hereinafter, abbreviated as TMAH). Up to the present time, researchers have focused on searching for a substance having as high transparency and etching resistance at 193 nm as novolac resins. For example, researchers at the Bell Labs Research Center have enhanced etching resistance of photoresist copolymers by adding an alicyclic unit to the main chain. In addition, researchers at Fujitsu of Japan and Sipri of the United States are actively investigating methacrylate and acrylate compounds as photoresist polymers. However, these techniques have not solved the problem of etching resistance, and involve increased production costs resulting from the introduction of alicyclic groups into the polymer. In addition, the low adhesiveness exhibited by most prior art photoresists is disadvantageous in that photolithographic patterns cannot be established with integrated L/S patterns of 150 nm or less.

SUMMARY OF THE INVENTION

An object of the present invention is to solve the problems described above, and to provide novel monomers which can be used to form copolymers which have excellent adhesiveness and sensitivity, and which can be easily produced at low production cost, and to provide a process for preparing the monomers.

Another object of the present invention is to provide copolymers of the novel monomers, and a process for preparing the same.

Another object of the present invention is to provide photoresist compositions using the copolymers and a process for preparing the same.

Still another object of the present invention is to provide a semiconductor element produced by using the photoresist composition.

The present invention provides a novel compound represented by following Chemical Formula 1:

Chemical Formula 1

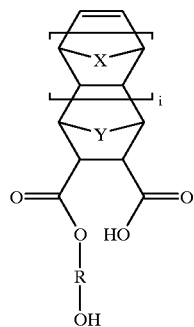

wherein,
R is substituted or non-substituted linear or branched ($C_1$–$C_{10}$)alkyl, substituted or non-substituted ($C_1$–$C_{10}$) ether, substituted or non-substituted ($C_1$–$C_{10}$)ester, or substituted or non-substituted ($C_1$–$C_{10}$)ketone,
X and Y are independently $CH_2$, $CH_2CH_2$, oxygen or sulfur; and
i is 0 or an integer of 1 to 2.

In order to achieve other technical objects, photoresist copolymer comprising repeating units of the monomer of Formula 1 are provided by another embodiment of the present invention. Preferred copolymers are represented by following Chemical Formulas 100 and 100a:

Chemical Formula 100

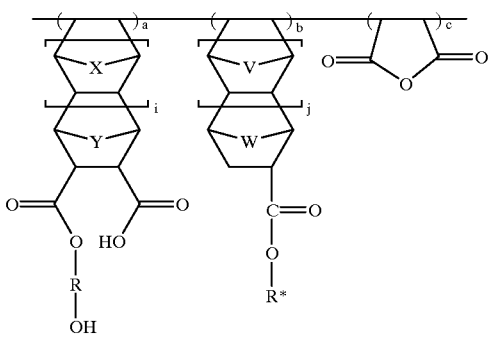

Chemical Formula 100a

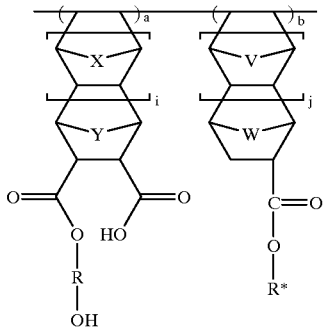

wherein,
R is substituted or non-substituted linear or branched ($C_1$–$C_{10}$)alkyl, substituted or non-substituted ($C_1$–$C_{10}$) ether, substituted or non-substituted ($C_1$–$C_{10}$)ester, or substituted or non-substituted ($C_1$–$C_{10}$)ketone;
X, Y, V and W are independently $CH_2$, $CH_2CH_2$, oxygen or sulfur;
i and j are independently 0 or an integer of 1 to 2;

R* is an acid-reactable group; and a, b and c represent the polymerization ratio of the monomers.

In the case of the chemical formula 100, it is preferred that a:b:c=(0.01–0.2): (0.1–0.4): 0.5 in molar equivalent ratio.

The photoresist composition according to the present invention comprises (i) a photoresist copolymer according to the present invention, a photoacid generator and a conventional organic solvent.

Hereinafter, the present invention will be described in detail.

DETAILED DESCRIPTION

Compounds of Chemical Formula 1 have been found to be particularly useful for preparing chemically amplified photoresist copolymers. Compounds of Chemical Formula 1 have a HYDROXY group which can enhance adhesiveness of the photoresist to a wafer substrate and a carboxylic acid group which can contribute to the enhancement of photosensitivity at the same time. In addition, the compounds can be simply synthesized without toxic odors and are readily crystallized in water without using any complicated separating means such as distillation or column chromatography. Thus, compounds of the present invention are advantageous in mass production at low cost.

In preferred compounds of Chemical Formula 1, R is represented by the following Chemical Formula 1a:

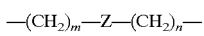   <Chemical Formula 1a> wherein

Z is a moiety of the formula —$C(R_1)(R_2)$— or oxygen;

$R_1$ and $R_2$ are independently H or an ($C_1$–$C_5$)alkyl; and m and n are independently 0 or an integer of 1 to 5.

The photoresist monomer according to the present invention can be prepared by reacting (i) a di-alcohol such as ethylene glycol, 1,3-propanediol, 1,4-butanediol, 1,5-pentanediol, 2,2-diethyl-1,3-propanediol, 2,2-dimethyl-1,3-propanediol and diethylene glycol and (ii) an anhydride such as 5-norbornene-2,3-dicarboxylic anhydride and exo-3,6-epoxy-1,2,3,6-tetrahydrophthalic anhydride, in an organic solvent such as tetrahydrofuran, dimethylformamide, dioxane, benzene and toluene.

For example, the compound represented by the following Chemical Formula 2, one of the compounds represented by the above Formula 1, can be obtained by reacting a compound of Chemical Formulas 2a and 2b in the presence of an acid catalyst or a base:

Chemical Formula 2

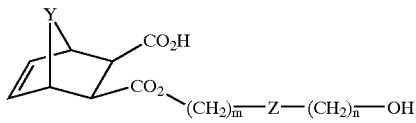

Chemical Formula 2a

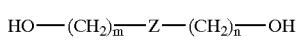

Chemical Formula 2b

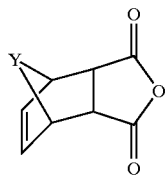

wherein,

Y is $CH_2$, $CH_2CH_2$, oxygen or sulfur;

Z is a moiety of the formula —$C(R_1)(R_2)$— or oxygen;

$R_1$ and $R_2$ are independently H or an ($C_1$–$C_5$)alkyl; and m and n are independently 0 or an integer of 1 to 5.

The compound of Chemical Formula 2a may be used in the same amount or in an excess amount relative to the compound of Chemical Formula 2b.

NaH, KH, $CaH_2$, $Na_2CO_3$, LDA (lithium diisopropylamide) or the like may be used as a base, and sulfuric acid, acetic acid or nitric acid may be used as an acid catalyst.

Novel monomers according to the present invention (the compounds represented by Chemical Formula 1) can also be prepared by a Diels-Alder reaction.

For example, the compound represented by the above chemical formula 2 can be prepared by following Reaction Schemes (1) and (2) below:

Reaction Scheme 1

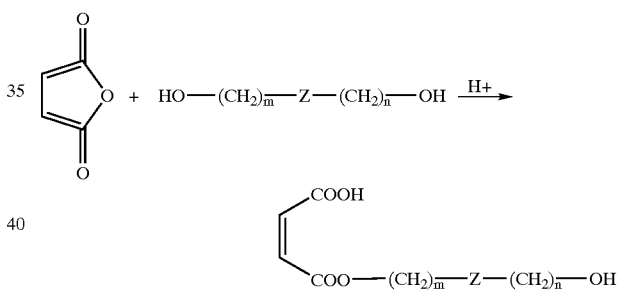

Reaction Scheme 2

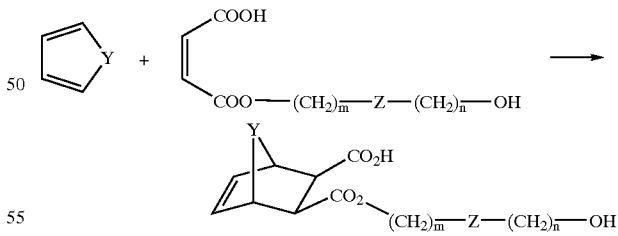

wherein

Y is $CH_2$, $CH_2CH_2$, oxygen or sulfur;

Z is a moiety of the formula —$C(R_1)(R_2)$— or oxygen;

$R_1$ and $R_2$ are independently H or an ($C_1$–$C_5$)alkyl; and m and n are independently 0 or an integer of 1 to 5.

That is, first, the intermediate material is obtained by reacting maleic anhydride and di-alcohol in an organic solvent such as benzene, tetrahydrofuran, dimethylformamide or dioxane in the presence of an acid catalyst, as shown in the Reaction Scheme 1, and then, the final product material is obtained by a Diels-Alder reaction which is performed in an organic solvent such as benzene and tetrahydrofuran, as shown in the Reaction Scheme 2.

Preferred photoresist copolymers according to the present invention comprise repeating units of a compound of Chemical Formula 1 as a first comonomer and a compound of the following Chemical Formula 3 as the second comonomer:

Chemical Formula 3

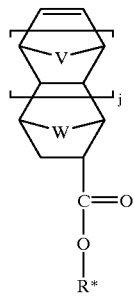

wherein,
V and W are independently $CH_2$, $CH_2CH_2$, oxygen or sulfur;
j is 0 or an integer of 1 to 2; and
R* is an acid reactable group.

In the Chemical Formula 3, the R* is released when it is reacted with the acid produced by the photoacid generator in the photoresist composition. Thus, while the photoresist polymer in exposed regions of the photoresist layer becomes soluble in the developing solution, the polymer in the unexposed regions is not dissolved in the developing solution because acid is not generated therein and therefore the acid-reactable groups are still bound to the photoresist polymer. As the result, a predetermined pattern is formed.

Accordingly, the compounds of Chemical Formula 3 have a role in enhancing the photosensitivity of the photoresist polymer by increasing the difference in solubility in the developing solution between the exposed portion and the unexposed portion.

Suitable acid-reactable (acid labile) groups include tert-butyl, 2-tetrahydrofuranyl, 2-tetrahydropyranyl, 2-ethoxyethyl, t-butoxyethyl and so on. In a most preferred embodiment, the second comonomer is tert-butyl-5-norbornene-2-carboxylate, the compound of following Chemical Formula 3a:

Chemical Formula 3a

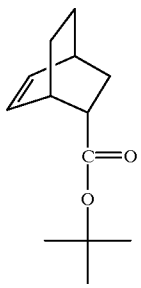

Maleic anhydride or maleimide derivatives can be added as polymerization-enhancing monomers for making the polymerization between the cycloolefin compounds more efficient. However, when performing polymerization using a metal catalyst, such a polymerization-enhancing monomer is not necessarily required.

The first comonomer of Formula 1 and the second comonomer of Formula 3 comprising the photoresist copolymer according to the present invention each contain substituents having large steric hindrance. Therefore, in preferred copolymers a spacer comonomer, such as the compound of the following Chemical Formula 4, is added to the main polymer chain in order not only to reduce the steric hindrance (thus increasing the synthetic yield, preferably to over 40%), but also to properly adjust the molecular weight to a desirable range (preferably, in the range of 7,000–8,000).

Chemical Formula 4

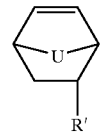

wherein,
U is $CH_2$, $CH_2CH_2$, oxygen or sulfur; and
R' is hydrogen or $C_1$–$C_5$ alkyl.
More preferred, the R' is hydrogen or methyl.

The following Chemical Formulas 100, 200, 100a and 200a represent preferred photoresist copolymers according to the present invention.

Chemical Formula 100

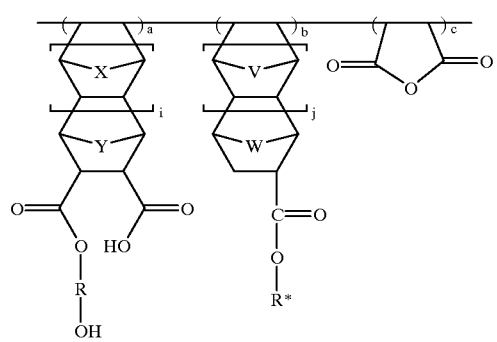

Chemical Formula 200

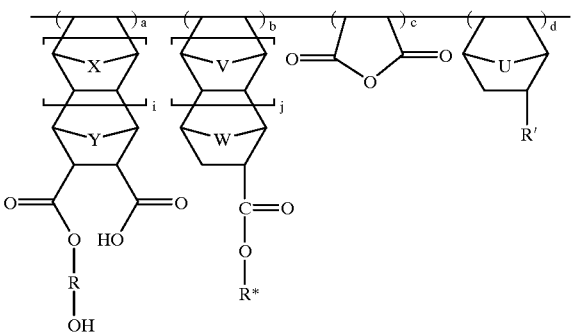

Chemical Formula 100a

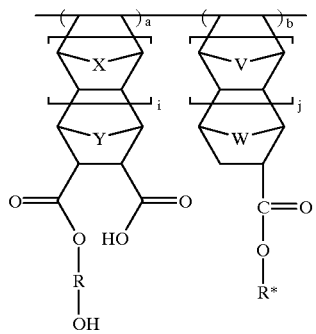

-continued

Chemical Formula 200a

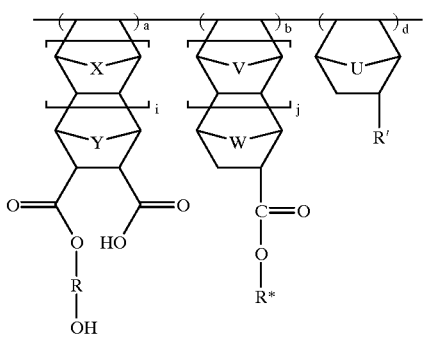

wherein,
X, Y, V, W and U are independently CH$_2$, CH$_2$CH$_2$, oxygen or sulfur;
R is substituted or non-substituted linear or branched (C$_1$–C$_{10}$) alkyl, substituted or non-substituted (C$_1$–C$_{10}$) ether, substituted or non-substituted (C$_1$–C$_{10}$)ester, or substituted or non-substituted (C$_1$–C$_{10}$)ketone;
R* is an acid-reactable group;
R' is hydrogen or C$_1$–C$_5$ alkyl;
i and j are independently 0 or an integer of 1 to 2; and
a, b, c and d are independently the polymerization ratio of the comonomers.

The molecular weight of the photoresist copolymers according the to present invention is 3,000 to 12,000, preferably, 5,000 to 10,000.

While the copolymers represented by the Chemical Formulas 100 and 200 are mainly obtained by a synthesizing method using a polymerization initiator, the copolymers represented by the Chemical Formulas 100a and 200a are mainly obtained by a synthesizing method using a metal catalyst.

A synthesizing method using a polymerization initiator is performed by reacting the comonomers in an organic solvent in the presence of a polymerization initiator. Presently preferred organic solvents include tetrahydrofuran, dimethylformamide, dimethyl sulfoxide, dioxane, methyl ethyl ketone, benzene, toluene or xylene may be used. Conventional radical polymerization initiators, such as 2,2-azobisisobutyronitrile (AIBN), acetyl peroxide, lauryl peroxide and tert-butyl peroxide may be used in the synthesis of the copolymers of the present invention.

Photoresist compositions according to the present invention, which are useful for photolithography processes employing a deep ultraviolet light source such as ArF, may be prepared by dissolving a photoresist copolymer according to the present invention together with a conventional photoacid generator in a conventional organic solvent.

Sulfide or onium type compounds are preferably used as the photoacid generator. The photoacid generator may be one or more compounds selected from the group consisting of diphenyl iodide hexafluorophosphate, diphenyl iodide hexafluoroarsenate, diphenyliodide hexafluoroantimonate, diphenyl p-methoxyphenyl triflate, diphenyl p-toluenyl triflate, diphenyl p-isobutylphenyl triflate, diphenyl p-tert-butylphenyl triflate, triphenylsulfonium hexafluorophosphate, triphenylsulfonium hexafluoroarsenate, triphenylsulfonium hexafluoroantimonate, triphenylsulfonium triflate and dibutylnaphthylsulfonium triflate. The photoacid generator is used in an amount of 0.05 to 10% by weight of the photoresist copolymer employed. If the amount of the photoacid generator is less than 0.05% by weight, photosensitivity of the photoresist becomes poor. On the other hand, if the amount is more than 10%, the photoacid generator readily absorbs deep ultraviolet to provide a pattern having poor cross-sectional surface.

A conventional organic solvent, such as ethyl 3-ethoxypriopionate, methyl 3-methoxypropionate, cyclohexanone, propylene glycol methyl ether acetate, or the like, may be used in the photoresist compositions of the present invention. The amount of solvent used is 200 to 1000% by weight of the photoresist copolymer, in order to obtain a photoresist layer of desirable thickness. According to the experiments by the present inventors, when the amount of solvent is 600% by weight, a photoresist layer having a thickness of 0.5 µm is obtained.

A conventional photoresist pattern-forming method can be used with the photoresist composition prepared according to the present invention, for example as follows:

First, the photoresist composition of the present invention is spin-coated on a silicon wafer to form a thin film, which is then soft-baked (i.e. heated in an oven or on a hot plate at 70 to 200° C., preferably at 80 to 150° C. for 1 to 5 minutes), and exposed to light by using an exposing device employing a deep ultraviolet light source, such as ArF light and KrF light, which has a wavelength below 250 nm. Then, the wafer is post-baked (i.e. heated at 70 to 200° C., more preferably, 100 to 200° C.). Then, the wafer is impregnated in 2.38% aqueous TMAH developing solution for 1.5 minutes, to obtain a photoresist image.

In the above procedure, the exposure energy is preferably 0.1 to 30 mJ/cm$^2$ and, instead of the deep ultraviolet light source, an E-beam, X-ray, EUV, VUV(Vacuum Ultra Violet) or similar light source may be used.

By employing the photoresist composition according to the present invention, a line/space (L/S) photoresist pattern having excellent adhesiveness and resolution is obtained, without pattern collapse, even when isolation is not more than 70 nm.

According to the present invention, a photoresist composition having excellent etching resistance and adhesiveness can be manufactured in large scale with low production cost, and a semiconductor element having excellent reliability can be prepared therefrom.

DETAILED DESCRIPTION OF PREFERRED EMBODIMENTS

The invention is described in more detail by referring to the examples below, but it should be noted that the present invention is by no means restricted to such examples.

Synthesis of Photoresist Monomer

Example 1

Synthesis of 5-norbornene-2-carboxylic acid-3-(2-hydroxyethyl) carboxylate

Ethylene glycol (0.1 mole) is added to 100 ml of tetrahydrofuran, and the mixture is chilled to −20° C. The chilled mixture is stirred for 20–30 minutes in the presence of a basic catalyst, for example, 0.1 mole of sodium hydride. Then, 0.1 mole of 5-norbornene-2,3-dicarboxylic anhydride is slowly added thereto, and the temperature is raised to room temperature to perform the reaction for 24 hours. When the reaction is completed, tetrahydrofuran is distilled off, and the residue is mixed with 0.2 N hydrochloric acid solution (500 ml), and the mixture is crystallized in a refrigerator for several days. Then, the resultant material is filtered, washed with cold water (100 ml), and dried to obtain the compound of Chemical Formula 11 as a pure a colorless solid (19.4 g / yield: 86%).

Chemical Formula 11

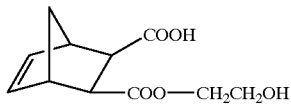

In the process described above, the crystallization step requires a long time (not less than a week). In order to solve the problem, the material resulting from the treatment with hydrochloric acid is extracted with 500 ml of ethyl acetate, dried over a dehydrating agent such as anhydrous magnesium sulfate and filtered. After evaporating the filtrate under reduced pressure, a white solid is obtained, which is then recrystallized from acetone / petroleum ether to provide the compound of Chemical Formula 11 in a pure state (17.6 g / yield: 78%).

Example 2

Synthesis of 5-norbornene-2-carboxylic acid-3-(3-hydroxypropyl) carboxylate

The procedure of Example 1 is repeated but using 1,3-propanediol instead of ethylene glycol as a reactant, to obtain the compound of Chemical Formula 12 as a colorless solid (21.1 g / yield: 88%).

Chemical Formula 12

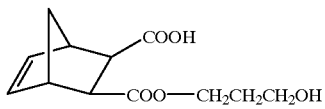

Example 3

Synthesis of 5-norbornene-2-carboxylic acid-3-(4-hydroxybutyl) carboxylate

The procedure of Example 1 is repeated but using 1,4-butanediol instead of ethylene glycol as a reactant, to obtain the compound of Chemical Formula 13 as a colorless solid (22.6 g / yield: 89%).

Chemical Formula 13

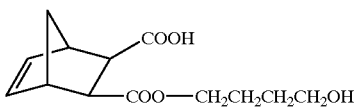

Example 4

Synthesis of 5-norbornene-2-carboxylic acid-3-(5-hydroxypentyl) carboxylate

The procedure of Example 1 is repeated but using 1,5-pentanediol instead of ethylene glycol as a reactant, to obtain the compound of Chemical Formula 14 as a colorless solid (22.8 g / yield: 85%).

Chemical Formula 14

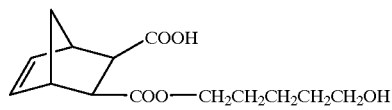

Example 5

Synthesis of 5-norbornene-2-carboxylic acid-3-[(2-ethyl-2-hydroxymethyl)butyl] carboxylate The procedure of Example 1 is repeated but using 2,2-diethyl-1,3-propanediol instead of ethylene glycol as a reactant, to obtain the compound of Chemical Formula 15 as a colorless solid (26.9 g / yield: 91%).

Chemical Formula 15

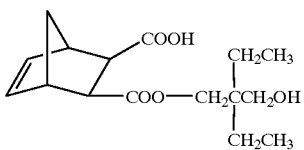

Example 6

Synthesis of 5-norbornene-2-carboxylic acid-3-(2,2-dimethyl-3-hydroxypropyl) carboxylate The procedure of Example 1 is repeated but using 2,2-dimethyl-1,3-propanediol instead of ethylene glycol as a reactant, to obtain the compound of Chemical Formula 16 as a colorless solid (24.1 g / yield: 90%).

Chemical Formula 16

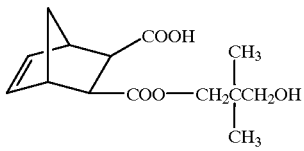

Example 7

Synthesis of 5-norbornene-2-carboxylic acid-3-[2-(2-hydroxyethoxy)ethyl] carboxylate The procedure of Example 1 is repeated but using diethylene glycol instead of ethylene glycol as a reactant, to obtain the compound of Chemical Formula 17 as a colorless solid (19.2 g / yield: 71%).

Chemical Formula 17

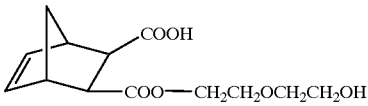

Example 8

Synthesis of oxabicyclo[2.2.1]-hept-5-ene-2-carboxylic acid-3-(2-hydroxyethyl) carboxylate Ethylene glycol (0.1 mole) is added to 100 ml of tetrahydrofuran, and the mixture is chilled to −20° C. To the chilled mixture, sodium hydride (0.1 mole) is added, and the resultant mixture is stirred for 20–30 minutes. Then, 0.1 mole of exo-3,6-epoxy-1,2,3,6-tetrahydrophthalic anhydride is slowly added thereto, and the temperature is raised to room temperature to perform the reaction for 24 hours. When the reaction is completed, tetrahydrofuran is distilled off, and the residue is mixed with 0.2 N hydrochloric acid solution (500 ml), and the mixture is crystallized in a refrigerator for several days. Then, the resultant material is filtered, washed with cold water (100 ml), and dried to obtain the compound of Chemical Formula 18 as a colorless solid (19.4 g / yield: 86%).

Chemical Formula 18

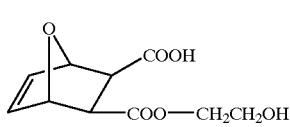

In the process for preparing the compound of Chemical Formula 18 described above, the crystallization step requires a long time of not less than a week. Thus, in order to solve the problem, the material resulting from the treatment with hydrochloric acid is extracted with 500 ml of ethyl acetate, dried over a dehydrating agent such as anhydrous magnesium sulfate, and filtered. After evaporating the filtrate under reduced pressure, a white solid is obtained, which is then recrystallized from acetone / petroleum ether to provide the compound of Chemical Formula 18 in a pure state (17.6 g / yield: 78%).

Example 9

Synthesis of oxabicyclo[2.2.1]hept-5-ene-2-carboxylic acid-3-(3-hydroxypropyl) carboxylate The procedure of Example 8 is repeated but using 1,3-propanediol instead of ethylene glycol as a reactant, to obtain the compound of Chemical Formula 19 as a colorless solid (20.8 g / yield: 86%).

Chemical Formula 19

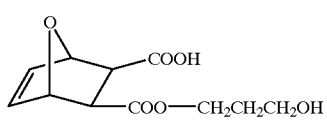

Example 10

Synthesis of oxabicyclo[2.2.1]hept-5-ene-2-carboxylic acid-3-(4-hydroxybutyl) carboxylate The procedure of Example 8 is repeated but using 1,4-butanediol instead of ethylene glycol as a reactant, to obtain the compound of Chemical Formula 20 as a colorless solid (22.3 g / yield: 87%).

Chemical Formula 20

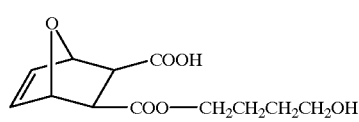

Example 11

Synthesis of oxabicyclo[2.2.1]hept-5-ene-2-carboxylic acid-3-hydroxypentyl carboxylate The procedure of Example 8 is repeated but using 1,5-pentanediol instead of ethylene glycol as a reactant, to obtain the compound of Chemical Formula 21 as a colorless solid (23.8 g / yield: 88%).

Chemical Formula 21

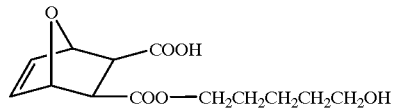

Example 12

Synthesis of oxabicyclo[2.2.1]hept-5-ene-2-carboxylic acid-3-[(2-ethyl-2-hydroxymethyl)butyl] carboxylate The procedure of Example 8 is repeated but using 2,2-diethyl-1,3-propanediol instead of ethylene glycol as a reactant, to obtain the compound of Chemical Formula 22 as a colorless solid (27.7 g / yield: 93%).

Chemical Formula 22

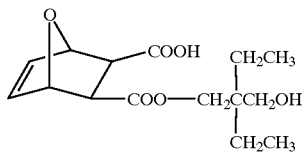

Example 13

Synthesis of oxabicyclo[2.2.1]hept-5-ene-2-carboxylic acid-3-(2,2-dimethyl-3-hydroxypropyl) carboxylate The procedure of Example 8 is repeated but using 2,2-dimethyl-1,3-propanediol instead of ethylene glycol as a reactant, to obtain the compound of Chemical Formula 23 as a colorless solid (23.6 g / yield: 86%).

Chemical Formula 23

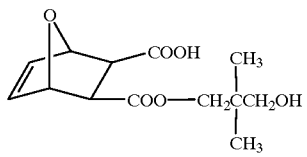

Example 14

Synthesis of oxabicyclo[2.2.1]hept-5-ene-2-carboxylic acid-3-[2-(2-hydroxyethoxy)ethyl] carboxylate The procedure of Example 8 is repeated but using diethylene glycol instead of ethylene glycol as a reactant, to obtain the compound of Chemical Formula 24 as a colorless solid (21.2 g / yield: 78%).

Chemical Formula 24

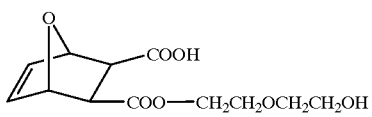

Synthesis of Photoresist Copolymer

Example 15

Synthesis of poly(5-norbornene-2-carboxylic acid-3-(2,2-diethyl-3-hydroxypropyl] carboxylate / tert-butyl 5-norbornene-2-carboxylate / maleic anhydride)

5-Norbornene-2-carboxylic acid-3-(2,2-diethyl-3-hydroxypropyl) carboxylate(0.2 mole), tert-butyl 5-norbornene-2-carboxylate(0.8 mole) and maleic anhydride (1.0 mole) are dissolved in tetrahydrofuran. Then, 0.5 to 10 g of AIBN (azobisisobutyronitrile) as a polymerization initiator is added thereto, and the resultant mixture is reacted at about 60–70° C. for 4 to 24 hours under nitrogen or argon atmosphere.

The polymer thus obtained is precipitated from ethyl ether or hexane, and dried to obtain the following compound of Chemical formula 101 (yield: 39%).

Chemical Formula 101

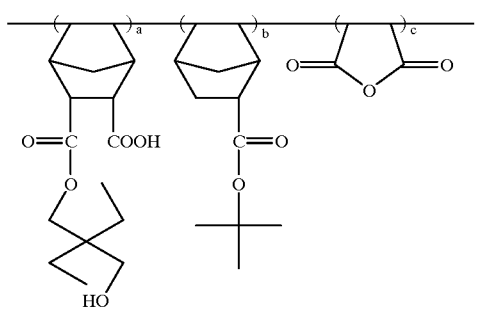

Example 16

Synthesis of poly[(mono-2-ethyl-2-hydroxymethylbutyl bicyclo[2,2,2]oct-5-ene-2,3-dicarboxylate) / tert-butyl 5-norbornene-2-carboxylate / maleic anhydride]

The procedure of Example 15 is repeated but using mono-2-ethyl-2-hydroxymethylbutyl bicyclo[2,2,2]oct-5-ene-2,3-dicarboxylate (0.2 mole) instead of 5-norbornene-2-carboxylic acid-3-(2,2-diethyl-3-hydroxypropyl) carboxylate (0.2 mole), to obtain the compound represented by the following Chemical Formula 102. (yield: 36%).

Chemical Formula 102

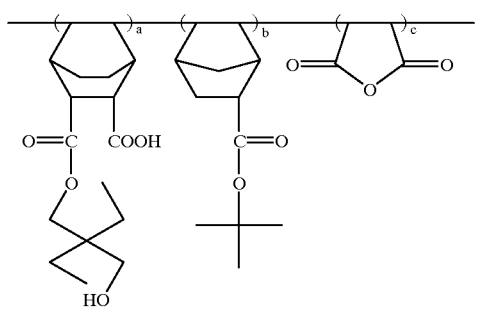

Example 17

Synthesis of poly(5-norbornene-2-carboxylic acid-3-(2,2-diethyl-3hydroxypropyl) carboxylate / tert-butyl bicyclo[2,2,2]oct-5-endo-2-carboxylate / maleic anhydride)

The procedure of Example 15 is repeated but using tert-butyl bicyclo[2,2,2]oct-5-endo-2-carboxylate (0.8 mole) instead of tert-butyl 5-norbornene-2-carboxylate (0.8 mole), to obtain the following compound represented by Chemical Formula 103. (yield: 38%).

Chemical Formula 103

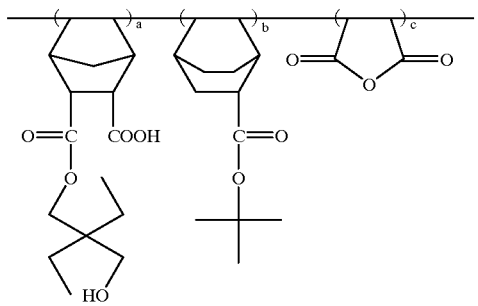

Example 18

Synthesis of poly[(mono-2-ethyl-2-hydroxymethylbutyl bicyclo[2,2,2]oct-5-ene-2,3-dicarboxylate) / tert-butyl bicyclo[2,2,2]oct-5-endo-2-carboxylate / maleic anhydride)]

The procedure of Example 16 is repeated but using tert-butyl bicyclo[2,2,2]oct-5-endo-2-carboxylate (0.8 mole) instead of tert-butyl 5-norbornene-2-carboxylate (0.8 mole), to obtain the following compound represented by Chemical Formula 104. (yield: 42%).

Chemical Formula 104

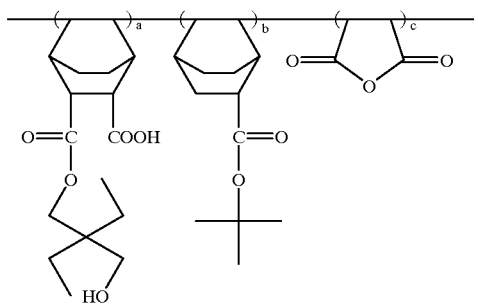

Example 19

Synthesis of poly(5-norbornene-2-carboxylic acid-3-(2-hydroxyethyl) carboxylate / tert-butyl-5-norbornene-2-carboxylate/ maleic anhydride / norbornene)

In 25 ml of tetrahydrofuran, 5-norbornene-2-carboxylic acid-(2-hydroxyethyl)carboxylate (10 mmol), maleic anhydride (100 mmol), norbornene (20 mmol), tert-butyl-5-norbornene-2-carboxylate (70 mmol) and AIBN (0.30 g) are dissolved, and the solution is reacted at 65° C. for 10 hours. When the reaction is completed, the reaction mixture is poured into a solvent for crystallization, such as petroleum ether, to obtain a pure solid, which is then filtered off and dried to give the compound of Chemical Formula 105. (11.3 g / yield: 42%).

Chemical Formula 105

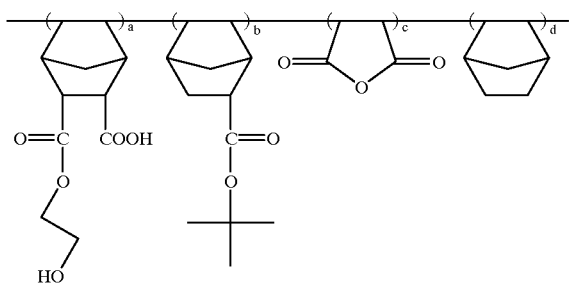

Example 20

Synthesis of poly(5-norbornene-2-carboxylic acid-3-(3-hydroxypropyl) carboxylate / tert-butyl-5-norbornene-2-carboxylate/ maleic anhydride / norbornene)

The procedure of Example 19 is repeated but using 5-norbornene-2-carboxylic acid-3-(3-hydroxypropyl) carboxylate as a reactant, instead of 5-norbornene-2-carboxylic acid-3-(2hydroxyethyl) carboxylate, to obtain the compound represented by Chemical Formula 106 as a colorless solid (11.58 g / yield: 41%).

Chemical Formula 106

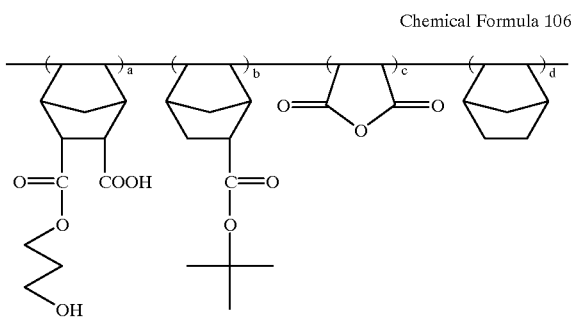

Example 21

Synthesis of poly(5-norbornene-2-carboxylic acid-3-(4-hydroxybutyl) carboxylate / tert-butyl-5-norbornene-2-carboxylate/ maleic anhydride / norbornene)

The procedure of Example 19 is repeated but using 5-norbornene-2-carboxylic acid-3-(4-hydroxybutyl) carboxylate as a reactant, instead of 5-norbornene-2-carboxylic acid-3-(2hydroxyethyl) carboxylate to obtain the compound represented by Chemical Formula 107 as a colorless solid (11.36 g / yield: 40%).

Chemical Formula 107

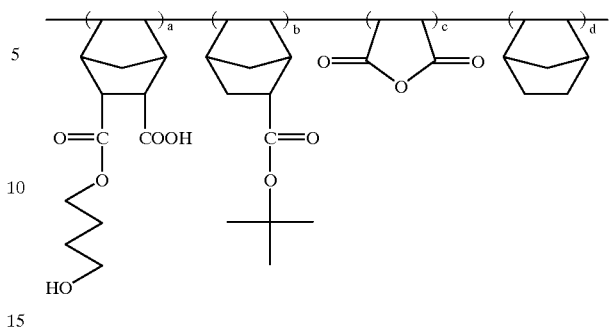

Example 22

Synthesis of poly(5-norbornene-2-carboxylic acid-3-(5hydroxypentyl) carboxylate / tert-butyl-5-norbornene-2-carboxylate/ maleic anhydride / norbornene)

The procedure of Example 19 is repeated but using 5-norbornene-2-carboxylic acid-3-(5-hydroxypentyl) carboxylate as a reactant, instead of 5-norbornene-2-carboxylic acid-3-(2-hydroxyethyl) carboxylate to obtain the compound represented by following Chemical Formula 108 as a colorless solid (11.7 g / yield: 41%).

Chemical Formula 108

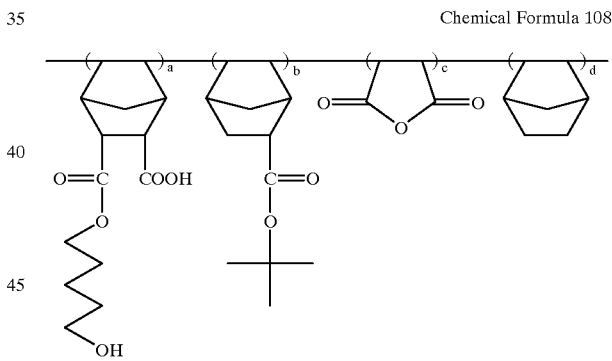

Example 23

Synthesis of poly(5-norbornene-2-carboxylic acid-3-[(2-ethyl-2-hydroxymethyl)butyl] carboxylate / tert-butyl-5-norbornene-2-carboxylate/ maleic anhydride / norbornene)

The procedure of Example 19 is repeated but using 5-norbornene-2-carboxylic acid-3-(2,2, -diethyl-3-hydroxypropyl) carboxylate as a reactant, instead of 5-norbornene-2-carboxylic acid-3-(2-hydroxyethyl) carboxylate to obtain the compound represented by following Chemical Formula 109 as a colorless solid (27.6 g / yield: 45%).

Chemical Formula 109

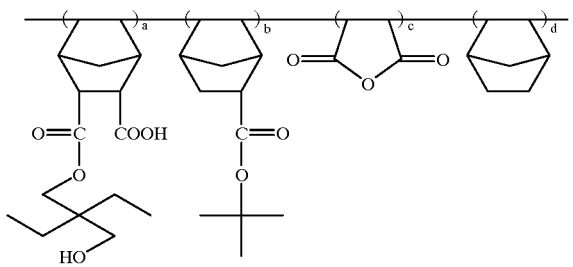

Example 24

Synthesis of poly(5-norbornene-2-carboxylic acid-3-(2,2-dimethyl-3-hydroxypropyl) carboxylate / tert-butyl-5-norbornene-2-carboxylate/ maleic anhydride / norbornene)

The procedure of Example 19 is repeated but using 5-norbornene-2-carboxylic acid-3-(2,2,-dimethyl-3-hydroxypropyl) carboxylate as a reactant, instead of 5-norbornene-2-carboxylic acid-3-(2-hydroxyethyl) carboxylate to obtain the compound represented by following Chemical Formula 110 as a colorless solid (11.7 g / yield: 43%).

Chemical Formula 110

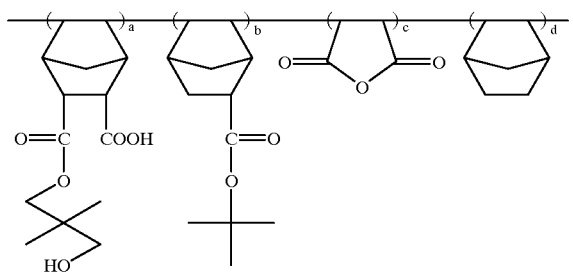

Example 25

Synthesis of poly(5-norbornene-2-carboxylic acid-3-[2(2-hydroxyethoxy)ethyl] carboxylate / tert-butyl-5-norbornene-2-carboxylate/ maleic anhydride / norbornene)

The procedure of Example 19 is repeated but using 5-norbornene-2-carboxylic acid-3-[2(2-hydroxyethoxy)ethyl] carboxylate as a reactant, instead of 5-norbornene-2-carboxylic acid-3-(2-hydroxyethyl) carboxylate to obtain the compound represented by following Chemical Formula 111 as a colorless solid (10.9 g / yield: 39%).

Chemical Formula 111

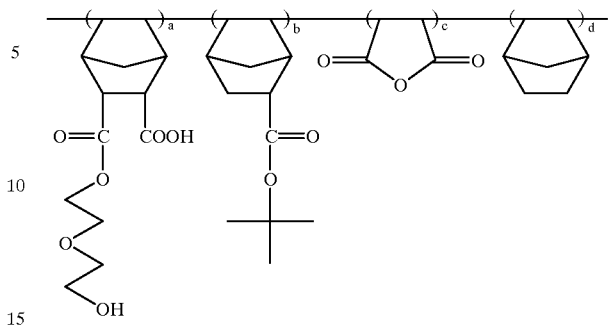

Example 26

Synthesis of poly(oxabicyclo[2.2.1]hept-5-ene-2-carboxylic acid-3-(2-hydroxyethyl) carboxylate / tert-butyl-5-norbornene-2-carboxylate/ maleic anhydride / norbornene)

In 25 ml of tetrahydrofuran, oxabicyclo[2.2.1]oct-5-ene-2-carboxylic acid-3-(2-hydroxyethyl) carboxylate (10 mmol), maleic anhydride (100 mmol), norbornene (20 mmol), tert-butyl-5-norbornene-2-carboxylate (70 mmol) and AIBN (0.30 g) are dissolved, and the solution is reacted at 65° C. for 10 hours. After the reaction is completed, the reaction mixture is poured into diethyl ether to obtain a pure solid, which is then dried to give the compound represented by following Chemical Formula 112 (11 g / yield: 41%).

Chemical Formula 112

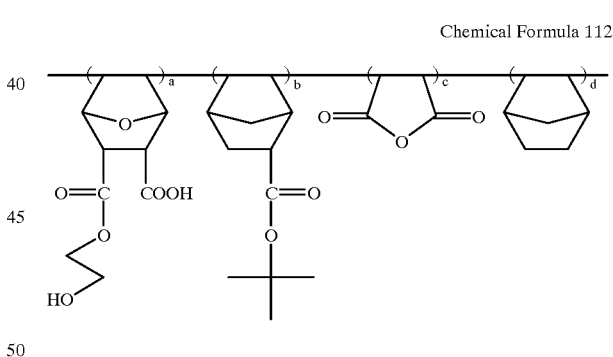

Example 27

Synthesis of poly(oxabicyclo[2.2.1]hept-5-ene-2-carboxylic acid-3-(3-hydroxypropyl) carboxylate / maleic anhydride / norbornene / tert-butyl-5-norbornene-2-carboxylate)

The procedure of Example 26 is repeated but using oxabicyclo[2.2.1]oct-5-ene-2-carboxylic acid-3-(3-hydroxypropyl) carboxylate instead of oxabicyclo[2.2.1]oct-5-ene-2-carboxylic acid-3-(2-hydroxyethyl) carboxylate to obtain the compound represented by following Chemical Formula 113 as a colorless solid (11.3 g / yield: 42%).

Chemical Formula 113

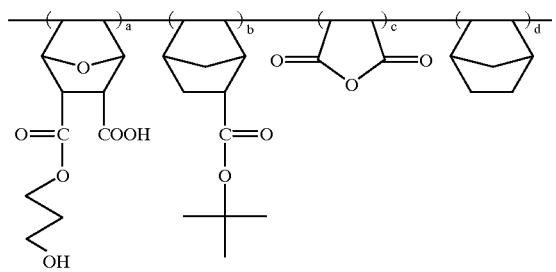

Example 28

Synthesis of poly(oxabicyclo[2.2.1]hept-5-ene-2-carboxylic acid-3-(4-hydroxybutyl) carboxylate / tert-butyl-5-norbornene-2-carboxylate/ maleic anhydride / norbornene)

The procedure of Example 26 is repeated but using oxabicyclo[2.2.1]oct-5-ene-2-carboxylic acid-3-(4-hydroxybutyl) carboxylate instead of oxabicyclo[2.2.1]oct-5-ene-2-carboxylic acid-3-(2-hydroxyethyl) carboxylate to obtain the compound represented by following Chemical Formula 114 as a colorless solid (11.1 g / yield: 42%).

Chemical Formula 114

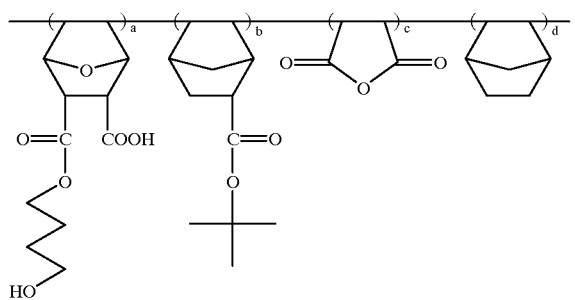

Example 29

Synthesis of poly(oxabicyclo[2.2.1]hept-5-ene-2-carboxylic acid-3-(5-hydroxypentyl) carboxylate / tert-butyl-5-norbornene-2-carboxylate/ maleic anhydride / norbornene)

The procedure of Example 26 is repeated but using oxabicyclo[2.2.1]oct-5-ene-2-carboxylic acid-3-(5-hydroxypentyl) carboxylate as a reactant, instead of oxabicyclo[2.2.1]oct-5-ene-2-carboxylic acid-3-(2-hydroxyethyl) carboxylate to obtain the compound represented by following Chemical Formula 115 as a colorless solid (10.9 g / yield: 40%).

Chemical Formula 115

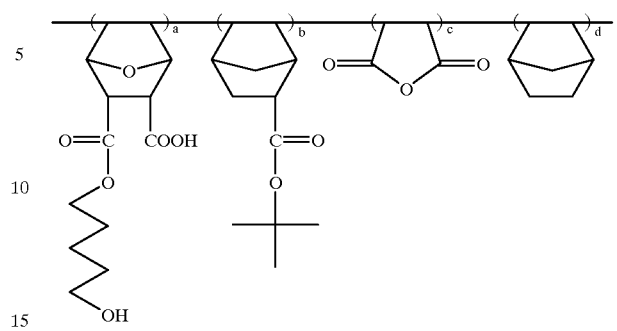

Example 30

Synthesis of poly(oxabicyclo[2.2.1]hept-5-ene-2-carboxylic acid-3-(2,2-diethyl-3-hydroxypropyl) carboxylate / tert-butyl-5-norbornene-2-carboxylate/ maleic anhydride / norbornene)

The procedure of Example 26 is repeated but using oxabicyclo[2.2.1]oct-5-ene-2-carboxylic acid-3-(2,2-diethyl-3-hydroxypropyl) carboxylate as a reactant, instead of oxabicyclo[2.2.1]oct-5-ene-2-carboxylic acid-3-(2-hydroxyethyl) carboxylate to obtain the compound represented by following Chemical Formula 116 as a colorless solid (12.1 g / yield: 44%).

Chemical Formula 116

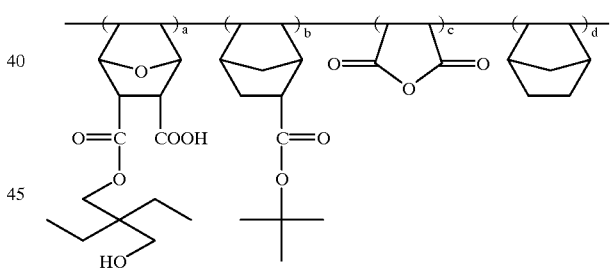

Example 31

Synthesis of poly(oxabicyclo[2.2.1]hept-5-ene-2-carboxylic acid-3-(2,2-dimethyl-3-hydroxypropyl) carboxylate / tert-butyl-5-norbornene-2-carboxylate/ maleic anhydride / norbornene)

The procedure of Example 26 is repeated but using oxabicyclo[2.2.1]oct-5-ene-2-carboxylic acid-3-(2,2-dimethyl-3-hydroxypropyl) carboxylate as a reactant, instead of oxabicyclo[2.2.1]oct-5-ene-2-carboxylic acid-3-(2-hydroxyethyl) carboxylate to obtain the compound represented by following Chemical Formula 117 as a colorless solid (11.7 g / yield: 43%).

Chemical Formula 117

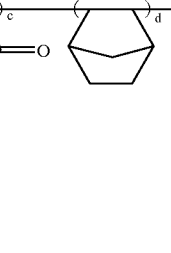

Example 32

Synthesis of poly(oxabicyclo[2.2.1]hept-5-ene-2-carboxylic acid-3-[2(2-hydroxyethoxy)ethy] carboxylate / tert-butyl-5-norbornene-2-carboxylate/ maleic anhydride / norbornene)

The procedure of Example 26 is repeated but using oxabicyclo[2.2.1]oct-5-ene-2-carboxylic acid-3-[2-(2-hydroxyethoxy)ethy] carboxylate as a reactant, instead of oxabicyclo[2.2.1]oct-5-ene-2-carboxylic acid-3-(2-hydroxyethyl) carboxylate to obtain the compound represented by following Chemical Formula 118 as a colorless solid (10.7 g / yield: 39%).

Chemical Formula 118

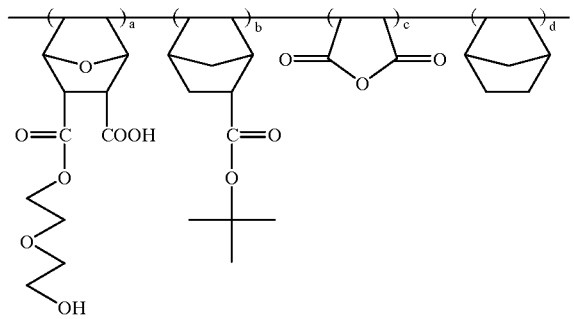

In the Examples described above, petroleum ether or diethyl ether is employed as a solvent for crystallization. Alternatively, alcohols such as methanol, ethanol and isopropanol may be employed.

Preparation of Photoresist Composition and Formation of Photoresist Pattern

Example 33

10 g of poly(5-norbornene-2-carboxylic acid-3-(2,2-diethyl-3-hydroxypropyl) carboxylate / tert-butyl 5-norbornene-2-carboxylate / maleic anhydride) obtained from the Example 15 is dissolved in 40 g of 3-methoxymethyl propionate, and triphenylsulfonium triflate or dibutyl naphthyl sulfonium triflate(0.01–1 g) is added thereto as a photoacid generator. After stirring, the resultant mixture is filtered through a 0.10 μm filter to obtain a photoresist composition. The photoresist composition thus obtained is coated in about 0.3 μm thickness on a surface, and exposed to light by using 193 nm of ArF light source. Then the photoresist is post-baked, and the semiconductor element is impregnated in 2.38% aqueous tetramethylammonium hydroxide (TMAH) solution to be developed and thus 0.13 μm L/S pattern is obtained.

Example 34

The procedure of Example 33 is repeated but using the photoresist copolymer obtained from the Example 16 instead of that obtained from the Example 15 and thus a 0.13 μm L/S pattern is obtained.

Example 35

The copolymer obtained from Example 19 (10 g) and triphenylsulfonium triflate (0.12 g) as a photoacid generator are dissolved in ethyl 3-ethoxypropionate solvent (60 g), and the resultant mixture is filtered through a 0.10 μm filter to prepare a photoresist solution. The photoresist solution thus prepared is spin-coated on a silicon wafer, and soft-baked at 110° C. for 90 seconds. After baking, the wafer is irradiated with light exposure energy of 0.1 to 10 mJ/cm² by using an ArF laser exposer, and the wafer is post-baked again at 110° C. for 90 seconds. When the post-baking is completed, it is developed in 2.38 wt % aqueous TMAH (tetramethylammonium hydroxide) solution for 40 seconds, to obtain a 0.11 μm L/S pattern.

Example 36

The procedure according to Example 35 is repeated but using the same amount of the copolymer obtained from Example 20 instead of the copolymer of Example 19, to obtain 0.13 μm L/S pattern.

Example 37

The procedure according to Example 35 is repeated but using the same amount of the copolymer obtained from Example 21 instead of the copolymer of Example 19, to obtain a 0.13 μm L/S pattern.

Example 38

The procedure according to Example 35 is repeated but using the same amount of the copolymer obtained from Example 22 instead of the copolymer of Example 19, to obtain a 0.13 μm L/S pattern.

Example 39

The procedure according to Example 35 is repeated but using the same amount of the copolymer obtained from Example 23 instead of the copolymer of Example 19, to obtain a 0.13 μm L/S pattern.

Example 40

The procedure according to Example 35 is repeated but using the same amount of the copolymer obtained from Example 24 instead of the copolymer of Example 19, to obtain a 0.13 μm L/S pattern.

Example 41

The procedure according to Example 35 is repeated but using the same amount of the copolymer obtained from Example 25 instead of the copolymer of Example 19, to obtain a 0.12 μm L/S pattern.

Example 42

The procedure according to Example 35 is repeated but using the same amount of the copolymer obtained from Example 26 instead of the copolymer of Example 19, to obtain a 0.12 μm L/S pattern.

Example 43

The procedure according to Example 35 is repeated but using the same amount of the copolymer obtained from Example 27 instead of the copolymer of Example 19, to obtain a 0.11 μm L/S pattern.

Example 44

The procedure according to Example 35 is repeated but using the same amount of the copolymer obtained from Example 28 instead of the copolymer of Example 19, to obtain a 0.13 μm LIS pattern.

Example 45

The procedure according to Example 35 is repeated but using the same amount of the copolymer obtained from Example 29 instead of the copolymer of Example 19, to obtain a 0. 13 μm L/S pattern.

Example 46

The procedure according to Example 35 is repeated but using the same amount of the copolymer obtained from Example 30 instead of the copolymer of Example 19, to obtain a 0. 12 μm L/S pattern.

Example 47

The procedure according to Example 35 is repeated but using the same amount of the copolymer obtained from Example 31 instead of the copolymer of Example 19, to obtain a 0. 13 μm L/S pattern.

Example 48

The procedure according to Example 35 is repeated but using the same amount of the copolymer obtained from Example 32 instead of the copolymer of Example 19, to obtain a 0.13 μm L/S pattern.

What is claimed is:

1. A photoresist polymer comprising at least one monomer represented by the Chemical Formula 1 below:

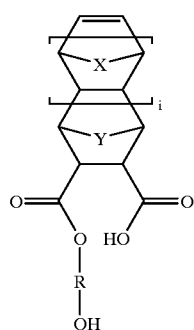

Chemical Formula 1 wherein,

R is substituted or non-substituted linear or branched $(C_1-C_{10})$alkyl, substituted or non-substituted $(C_1-C_{10})$ ether, substituted or non-substituted $(C_1-C_{10})$ester, or substituted or non-substituted $(C_1-C_{10})$ketone;

X and Y are independently $CH_2$, $CH_2CH_2$, oxygen or sulfur; and i is 0 or an integer of 1 to 2.

2. A photoresist polymer according to claim 1 further comprising a second comonomer represented by the Chemical Formula 3:

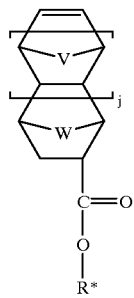

Chemical Formula 3 wherein,

V and W are independently $CH_2$, $CH_2CH_2$, oxygen or sulfur;

R* is an acid-reactable group; and j is 0 or an integer of 1 to 2.

3. A photoresist copolymer according to the claim 2, wherein said R* is tert-butyl, 2-tetrahydrofuranyl, 2-tetrahydropyranyl, 2-ethoxyethyl or t-butoxyethyl.

4. A photoresist copolymer according to the claim 2, wherein said i=j=0.

5. A photoresist copolymer according to the claim 2, wherein said compound represented by the following Chemical Formula 3 is tert-butyl-5-norbornene-2-carboxylate, the compound of following Chemical Formula 3a or the compound of following Chemical Formula 3b:

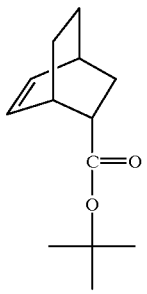

Chemical Formula 3a

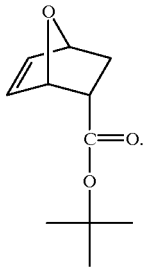

Chemical Formula 3b

6. A photoresist copolymer according to the claim 2, further comprising a polymerization-enhancing monomer selected from the group consisting of maleic anhydride and maleimide derivatives.

7. A photoresist copolymer according to the claim 2, said photoresist copolymer further comprising a spacer material represented by the following Chemical Formula 4

Chemical Formula 4

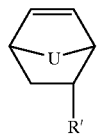

wherein,

U is $CH_2$, $CH_2CH_2$, oxygen or sulfur; and

R' is hydrogen or $C_1-C_5$ alkyl.

8. A photoresist copolymer according to the claim 2, wherein said photoresist copolymer is selected from the group consisting of the following Chemical Formulas 100, 200, 100a and 200a Chemical Formula 100

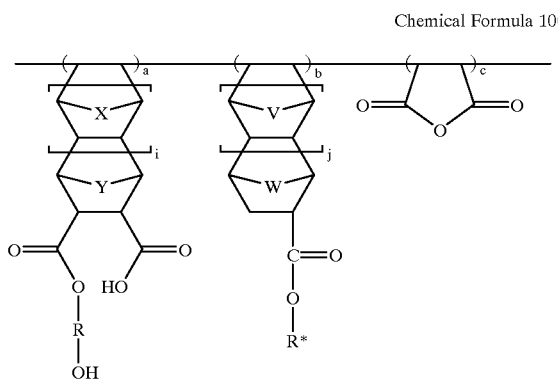

Chemical Formula 200

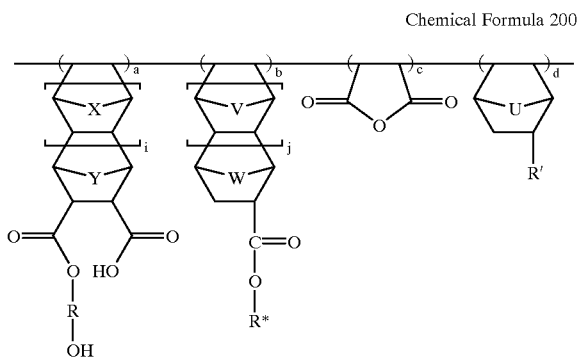

Chemical Formula 100a

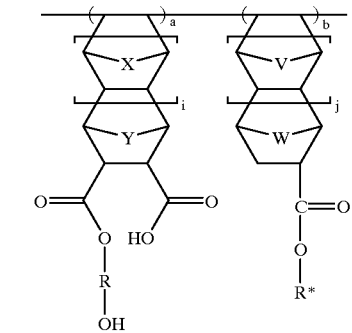

Chemical Formula 200a

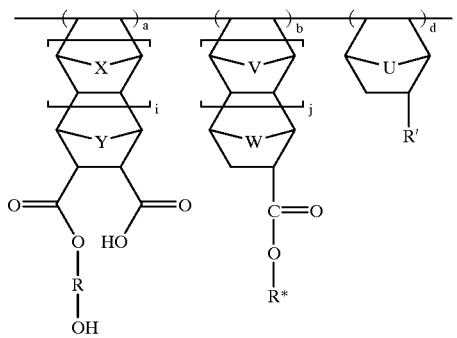

wherein,

X, Y, V, W and U are independently $CH_2$, $CH_2CH_2$, oxygen or sulfur;

R is substituted or non-substituted linear or branched $(C_1-C_{10})$alkyl, substituted or non-substituted $(C_1-C_{10})$ ether, substituted or non-substituted $(C_1-C_{10})$ester, or substituted or non-substituted $(C_1-C_{10})$ketone;

R* is an acid-reactable group;

R' is hydrogen or $C_1-C_5$ alkyl;

i and j are independently 0 or an integer of 1 to 2; and a, b, c and d are independently the polymerization ratios of the monomers.

9. A photoresist copolymer according to the claim 2, wherein said photoresist copolymer is selected from the group consisting of poly(5-norbornene-2-carboxylic acid-3-(2,2-diethyl)-hydroxypropyl carboxylate / tert-butyl 5-norbornene-2-carboxylate / maleic anhydride);

poly(mono-2-ethyl-2-hydroxymethylbutyl bicyclo[2,2,2]oct-5-ene-2,3-dicarboxylate / tert-butyl 5-norbornene-2-carboxylate / maleic anhydride);

poly(5-norbornene-2-carboxylic acid-3-(2,2-diethyl)-hydroxypropyl carboxylate / tert-butyl bicyclo[2,2,2]oct-5-endo-2-carboxylate / maleic anhydride)

poly(mono-2-ethyl-2-hydroxymethylbutyl bicyclo[2,2,2]oct-5-ene-2,3-dicarboxylate / tert-butyl bicyclo[2,2,2]oct-5-endo-2-carboxylate / maleic anhydride);

poly(5-norbornene-2-carboxylic acid-3-hydroxyethyl carboxylate / tert-butyl-5-norbornene-2-carboxylate/ maleic anhydride / norbornene);

poly(5-norbornene-2-carboxylic acid-3-hydroxypropyl carboxylate / tert-butyl-5-norbornene-2-carboxylate/ maleic anhydride / norbornene);

poly(5-norbornene-2-carboxylic acid-3-hydroxybutyl carboxylate / tert-butyl-5-norbornene-2-carboxylate/ maleic anhydride / norbornene);

poly(5-norbornene-2-carboxylic acid-3-hydroxypentyl carboxylate / tert-butyl-5-norbornene-2-carboxylate/ maleic anhydride / norbornene);

poly(5-norbornene-2-carboxylic acid-3-(2-ethyl-2-hydroxymethyl)butyl carboxylate / tert-butyl-5-norbornene-2-carboxylate/ maleic anhydride / norbornene);

poly(5-norbornene-2-carboxylic acid-3-(2,2-dimethyl)hydroxypropyl carboxylate / tert-butyl-5-norbornene-2-carboxylate/ maleic anhydride / norbornene);

poly(5-norbornene-2-carboxylic acid-3-(2-hydroxyethoxy)ethyl carboxylate / tert-butyl-5- norbornene-2-carboxylate/ maleic anhydride / norbornene);

poly(oxabicyclo[2.2.1]hept-5-ene-2-carboxylic acid-3-hydroxyethyl carboxylate / tert-butyl-5-norbornene-2-carboxylate/ maleic anhydride / norbornene);

poly(oxabicyclo[2.2.1]hept-5-ene-2-carboxylic acid-3-hydroxypropyl carboxylate / maleic anhydride / norbornene/tert-butyl-5-norbornene-2-carboxylate);

poly(oxabicyclo[2.2.1]hept-5-ene-2-carboxylic acid-3-hydroxybutyl carboxylate / tert-butyl-5-norbodene-2-carboxylate/ maleic anhydride / norbornene);

poly(oxabicyclo[2.2.1]hept-5-ene-2carboxylic acid-3-hydroxypentyl carboxylate / tert-butyl-5-norbornene-2-carboxylate/ maleic anhydride / norbornene);

poly(oxabicyclo[2.2.1]hept-5-ene-2-carboxylic acid-3-(2,2-diethyl)hydroxypropyl carboxylate / tert-butyl-5-norbornene-2-carboxylate/ maleic anhydride / norbornene);

poly(oxabicyclo[2.2.1]hept-5-ene-2-carboxylic acid-3-(2,2-dimethyl)hydroxypropyl carboxylate / tert-butyl-5-norbornene-2-carboxylate/ maleic anhydride / norbornene); and poly(oxabicyclo[2.2.1]hept-5-ene-2-carboxylic acid-3-(2-ethoxy)ethanol carboxylate / tert-butyl-5-norbornene-2-carboxylate/ maleic anhydride / norbornene).

* * * * *

UNITED STATES PATENT AND TRADEMARK OFFICE
CERTIFICATE OF CORRECTION

PATENT NO. : 6,410,670 B1
DATED : June 25, 2002
INVENTOR(S) : Geun Su Lee et al.

It is certified that error appears in the above-identified patent and that said Letters Patent is hereby corrected as shown below:

Column 4,
Lines 32-40, please replace Reaction Scheme 1 with the following Reaction Scheme 1:

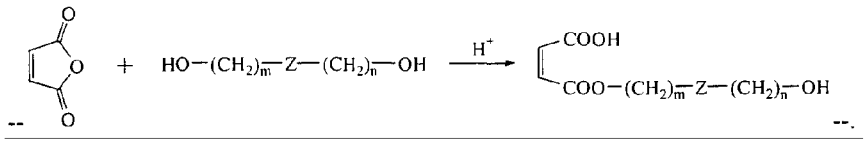

Column 13,
Lines 62-65, please replace the title with the following title:
-- Synthesis of poly(5-norbornene-2-carboxylic acid-3-(2,2-diethyl-3-hydroxypropyl) carboxylate / tert-butyl bicyclo[2,2,2]oct-5-endo-2-carboxylate / maleic anhydride) --.

Column 14,
Lines 58-59, the phrase "In 25 ml of tetrahydrofuran, 5-norbornene-2-carboxylic acid-(2-hydroxyethyl)carboxylate (10 mmol)," should read -- In 25 ml of tetrahydrofuran, 5-norbornene-2-carboxylic acid-3-(2-hydroxyethyl)carboxylate (10 mmol), --.

Column 15,
Lines 31-32 and 64-65, the phrase "instead of 5-norbornene-2-carboxylic acid-3-(2hydroxyethyl) carboxylate," should read -- instead of 5-norbornene-2-carboxylic acid-3-(2-hydroxyethyl) carboxylate, --

Column 16,
Lines 22-25, please replace the title with the following title:
-- Synthesis of poly(5-norbornene-2-carboxylic acid-3-(5-hydroxypentyl) carboxylate / tert-butyl-5-norbornene-2-carboxylate/ maleic anhydride / norbornene) --.

Column 17,
Lines 55-59, please replace the title with the following title:
-- Synthesis of poly(5-norbornene-2-carboxylic acid-3-[2-(2-hydroxyethoxy)ethyl] carboxylate / tert-butyl-5-norbornene-2-carboxylate / maleic anhydride / norbornene) --.
Lines 63-64, the phrase "5-norbornene-2-carboxylic acid-3-[2(2-hydroxyethoxy)ethyl] carboxylate" should read -- 5-norbornene-2-carboxylic acid-3-[2-(2-hydroxyethoxy) ethyl] carboxylate --.

UNITED STATES PATENT AND TRADEMARK OFFICE
CERTIFICATE OF CORRECTION

PATENT NO.   : 6,410,670 B1
DATED        : June 25, 2002
INVENTOR(S)  : Geun Su Lee et al.

It is certified that error appears in the above-identified patent and that said Letters Patent is hereby corrected as shown below:

Column 21,
Lines 18-21, please replace the title with the following title:
-- Synthesis of poly(oxabicyclo[2.2.1]hept-5-ene-2-carboxylic acid-3-[2-(2-hydroxyethoxy)ethyl] caroxylate / tert-butyl-5-norbornene-2-carboxylate / maleic anhydride / norbornene) --.
Lines 24-25, the phrase "oxabicyclo[2.2.1]oct-5-ene-2-carboxylic acid-3-[2-(2-hydroxyethoxy)ethy] carboxylate" should read -- oxabicyclo[2.2.1]oct-5-ene-2-carboxylic acid-3-[2-(2-hydroxyethoxy)ethyl] carboxylate --.

Column 27,
Lines 9-11, the phrase "poly(oxabicyclo[2.2.1]hept-5-ene-2-carboxylic acid-3-hydroxybutyl carboxylate / tert-butyl-5-norbodene-2-carboxylate / maleic anhydride / norbornene);" should read -- poly(oxabicyclo[2.2.1]hept-5-ene-2-carboxylic acid-3-hydroxybutyl carboxylate / tert-butyl-5-norbornene-2-carboxylate / maleic anhydride / norbornene); --.

Signed and Sealed this

Thirty-first Day of August, 2004

JON W. DUDAS
*Director of the United States Patent and Trademark Office*

UNITED STATES PATENT AND TRADEMARK OFFICE
CERTIFICATE OF CORRECTION

PATENT NO. : 6,410,670 B1
DATED : June 25, 2002
INVENTOR(S) : Geun Su Lee et al.

It is certified that error appears in the above-identified patent and that said Letters Patent is hereby corrected as shown below:

Column 4,
Lines 32-40, please replace Reaction Scheme 1 with the following Reaction Scheme 1:

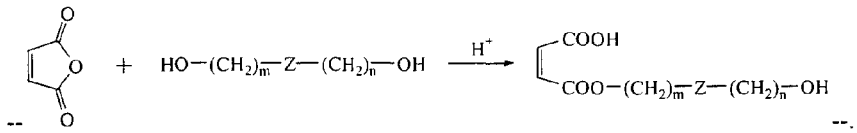

Column 13,
Lines 62-65, please replace the title with the following title:
-- Synthesis of poly(5-norbornene-2-carboxylic acid-3-(2,2-diethyl-3-hydroxypropyl) carboxylate / tert-butyl bicyclo[2,2,2]oct-5-endo-2-carboxylate / maleic anhydride) --.

Column 14,
Lines 58-59, the phrase "In 25 ml of tetrahydrofuran, 5-norbornene-2-carboxylic acid-(2-hydroxyethyl)carboxylate (10 mmol)," should read -- In 25 ml of tetrahydrofuran, 5-norbornene-2-carboxylic acid-3-(2-hydroxyethyl)carboxylate (10 mmol), --.

Column 15,
Lines 31-32 and 64-65, the phrase "instead of 5-norbornene-2-carboxylic acid-3-(2hydroxyethyl) carboxylate," should read -- instead of 5-norbornene-2-carboxylic acid-3-(2-hydroxyethyl) carboxylate, --

Column 16,
Lines 22-25, please replace the title with the following title:
-- Synthesis of poly(5-norbornene-2-carboxylic acid-3-(5-hydroxypentyl) carboxylate / tert-butyl-5-norbornene-2-carboxylate/ maleic anhydride / norbornene) --.

Column 17,
Lines 55-59, please replace the title with the following title:
-- Synthesis of poly(5-norbornene-2-carboxylic acid-3-[2-(2-hydroxyethoxy)ethyl] carboxylate / tert-butyl-5-norbornene-2-carboxylate / maleic anhydride / norbornene) --.
Lines 63-64, the phrase "5-norbornene-2-carboxylic acid-3-[2(2-hydroxyethoxy)ethyl] carboxylate" should read -- 5-norbornene-2-carboxylic acid-3-[2-(2-hydroxyethoxy) ethyl] carboxylate --.

UNITED STATES PATENT AND TRADEMARK OFFICE
CERTIFICATE OF CORRECTION

PATENT NO. : 6,410,670 B1
DATED : June 25, 2002
INVENTOR(S) : Geun Su Lee et al.

It is certified that error appears in the above-identified patent and that said Letters Patent is hereby corrected as shown below:

Column 21,
Lines 18-21, please replace the title with the following title:
-- Synthesis of poly(oxabicyclo[2.2.1]hept-5-ene-2-carboxylic acid-3-[2-(2-hydroxyethoxy)ethyl] carboxylic / tert-butyl-5-norbornene-2-carboxylate / maleic anhydride / norbornene) --.
Lines 24-25, the phrase "oxabicyclo[2.2.1]oct-5-ene-2-carboxylic acid-3-[2-(2-hydroxyethoxy)ethy] carboxylate" should read -- oxabicyclo[2.2.1]oct-5-ene-2-carboxylic acid-3-[2-(2-hydroxyethoxy)ethyl] carboxylate --.

Column 27,
Lines 9-11, the phrase "poly(oxabicyclo[2.2.1]hept-5-ene-2-carboxylic acid-3-hydroxybutyl carboxylate / tert-butyl-5-norbodene-2-carboxylate / maleic anhydride / norbornene);" should read -- poly(oxabicyclo[2.2.1]hept-5-ene-2-carboxylic acid-3-hydroxybutyl carboxylate / tert-butyl-5-norbornene-2-carboxylate / maleic anhydride / norbornene); --.

This certificate supersedes Certificate of Correction issued August 31, 2004.

Signed and Sealed this

Seventh Day of December, 2004

JON W. DUDAS
*Director of the United States Patent and Trademark Office*